United States Patent
Svennerholm et al.

(10) Patent No.: US 10,548,961 B2
(45) Date of Patent: Feb. 4, 2020

(54) VACCINE FOR PROTECTION AGAINST ETEC-INDUCED DIARRHEA COMPRISING DMLT

(71) Applicant: SCANDINAVIAN BIOPHARMA HOLDING AB, Solna (SE)

(72) Inventors: Ann-Mari Svennerholm, Västra Frölunda (SE); Joshua Tobias, Göteborg (SE); Nils Carlin, Bromma (SE); Jan Holmgren, Västra Frölunda (SE)

(73) Assignee: SCANDINAVIAN BIOPHARMA HOLDING AB, Solna (SE)

( * ) Notice: Subject to any disclaimer, the term of this patent is extended or adjusted under 35 U.S.C. 154(b) by 180 days.

(21) Appl. No.: 14/744,874

(22) Filed: Jun. 19, 2015

(65) Prior Publication Data
US 2015/0320850 A1    Nov. 12, 2015

Related U.S. Application Data

(63) Continuation of application No. 14/239,772, filed as application No. PCT/EP2011/065784 on Sep. 12, 2011, now abandoned.

(51) Int. Cl.
| | | |
|---|---|---|
| *A61K 39/108* | (2006.01) | |
| *A61K 45/00* | (2006.01) | |
| *A61K 47/00* | (2006.01) | |
| *A01N 63/00* | (2006.01) | |
| *A61K 48/00* | (2006.01) | |
| *A61K 9/00* | (2006.01) | |
| *A61K 39/00* | (2006.01) | |

(52) U.S. Cl.
CPC ........ *A61K 39/0258* (2013.01); *A61K 9/0053* (2013.01); *A61K 2039/521* (2013.01); *A61K 2039/542* (2013.01); *A61K 2039/55544* (2013.01); *A61K 2039/70* (2013.01); *Y02A 50/474* (2018.01)

(58) Field of Classification Search
CPC .... A61K 39/0258; A61K 38/00; A61K 39/39; A61K 35/74; C07K 14/245; C12N 15/86
See application file for complete search history.

(56) References Cited

FOREIGN PATENT DOCUMENTS

| WO | WO 92/14487 | 9/1992 |
|---|---|---|
| WO | WO 96/34893 | 11/1996 |
| WO | WO 99/47167 | 9/1999 |
| WO | WO 2007/089205 | 8/2007 |
| WO | WO 2009/004002 | 1/2009 |

OTHER PUBLICATIONS

Holmgren et al., Vaccine, 2013; 31: 2457-2464.*
Svennerholm, Indian J Med Res, 2011; 133: 188-194.*
Lundgren et al., Vaccine, 2013; 31: 1163-1170.*
Das et al., BMC Public Heath, 2013; 13(Suppl 3):S11—pp. 1-11.*
Lebens et al., "Synthesis of hybrid molecules between heat-labile enterotoxin and cholera toxin B subunits: potential for use in a broad-spectrum vaccine," Infec. Immun. (1996) 64(6,):2144-2150.
Norton et al., "Characterization of a mutant *Escherichia coli* heat-labile toxin, LT (R192G/L211A), as a safe and effective oral adjuvant," Clin. Vaccine Immunol. (2011) 18(4):546-551.
Svennerholm Ann-Mari, "From cholera to enterotoxigenic *Escherichia coli* (ETEC) vaccine development", Indian J. Med. Rex. (Feb. 2011) 133(2):188-194.
Svennerholm et al., "Vaccines against enterotoxigenic *Escherichia coli*" Expert Reviews (Aug. 2008) 7(6): 795-804.
Qadri et al., "Reduced doses of oral killed enterotoxigenic *Escherichia coli* plus cholera toxin B subunit vaccine is safe and immunogenic in Bangladeshi infants 6-17 months of ages: Dosing studies in different age groups" Vaccine (Mar. 2006) 24(10):1726-1733.
Tobias J. et al., "Construction of non-toxic *Escherichia coli* and Vibrio cholera strains expressing high and immunogenic levels of enterotoxigenic *E. coli* colonization factor I fimbriae" Vaccine (2007) 26(6):743-752.
Tobias et al., "Over-expression of major colonization factors of enterotoxigenic *Escherichia coli*, alone or together, on non-toxigenic *E. coli* bacteria" Vaccine (Oct. 8, 2010) 28(43):6977-6984.
Tobias et al., "Role of different genes in the CS6 operon for surface expression of Enterotoxigenic *Escherichia coli* colonization factor CS6" Vaccine (Oct. 3, 2008) 26(42):5373-5380.
Tobias et al., "Construction of a non-toxigenic *Escherichia coli* oral vaccine strain expressing large amounts of CS6 and inducing strong intestinal and serum anti-CS6 antibody responses in mice" Vaccine (Nov. 2011) 29(48):8863-8869.
International Search Report dated Jun. 20, 2012 for PCT Application No. PCT/EP2011/065784, filed Sep. 12, 2011.
Written Opinion dated Jul. 9, 2012 for PCT Application No. PCT/EP2011/065784, filed Sep. 12, 2011.
International Preliminary Report on Patentability dated Mar. 12, 2014 for PCT Application No. PCT/EP2011/065784, filed Sep. 12, 2011.

* cited by examiner

*Primary Examiner* — Gary B Nickol
*Assistant Examiner* — Lakia J Jackson-Tongue
(74) *Attorney, Agent, or Firm* — Knobbe, Martens, Olson & Bear LLP

(57) ABSTRACT

An oral vaccine for immunization against ETEC-induced diarrhea, comprising inactivated *Escherichia coli* cells expressing an ETEC colonization factor antigen and dmLT protein adjuvant, wherein the vaccine preferably comprises less than $10^{13}$ cells per unit dose.

15 Claims, 4 Drawing Sheets

VACCINE FOR PROTECTION AGAINST ETEC-INDUCED DIARRHEA COMPRISING DMLT

CROSS REFERENCE TO RELATED APPLICATIONS

This application is a U.S. National Phase Application of PCT International Application No. PCT/EP2011/065784, filed on Sep. 12, 2011, designating the U.S.A. and published in the English language. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList_NOV001_002C1.txt, the date of creation of the ASCII text file is Jun. 19, 2015, and the size of the ASCII text file is 3 KB.

TECHNICAL FIELD

The present invention relates to the field of killed oral whole-cell vaccines against ETEC-induced diarrhea.

BACKGROUND

Enterotoxigenic *E. coli* (ETEC) is one of the most frequent bacterial causes of diarrhea in children in developing countries. ETEC is also a major cause of traveler's diarrhea. Disease usually occurs following ingestion of ETEC and colonization of the intestinal mucosal surface. Colonization is facilitated by specific colonization factors (CF) located on the surface of the bacteria. Following colonization, the bacteria produce a heat-labile toxin (LT) and/or a heat stable toxin (ST) that trigger watery diarrhea. The objective of this invention is to develop an oral inactivated ETEC vaccine for use in children living in endemic areas as well as in Western travelers going to ETEC-endemic areas.

A previously developed oral vaccine consisting of inactivated ETEC bacteria and recombinant cholera toxin B-subunit (CTB) was shown to be safe and immunogenic in children living in endemic areas as well as in Western adults traveling to areas endemic for ETEC. This vaccine conferred some protection against moderate/severe diarrhea in adult travelers; however, the protective efficacy in children was not significant.

The inventors reviewed the information gained from the clinical studies of this 1$^{st}$ generation ETEC vaccine and concluded that a vaccine formulation containing increased amounts of CF antigens and with increased toxin neutralizing capacity should provide better protective immunity. One problem with simply increasing the amount of CF antigens is that too large number of cells in a vaccine dose result in adverse effects such as nausea and vomiting, in particular in infants.

Hence, a new 2$^{nd}$ generation, tetravalent ETEC vaccine was developed, containing four inactivated *E. coli* strains over-expressing, i.e. increased levels compared to clinical ETEC isolates, of the most prevalent CFs, i.e. CFA/I, CS3, CS5 and CS6, and a novel rLTB/CTB (LCTBA) hybrid protein "toxoid" with stronger immunogenicity against LT than the rCTB toxoid used in the previously studied formulation. A monovalent prototype of this 2$^{nd}$ generation vaccine was recently studied in a clinical phase I trial and was found to be immunogenic, safe and well tolerated by the subjects.

*E. coli* LT has both enterotoxic and adjuvant properties. However, the use of LT toxin as an oral adjuvant has been hampered by its enterotoxicity. To circumvent this problem, a double mutant LT (dmLT) toxoid, devoid of enterotoxicity but with retained adjuvant properties was recently developed. Safety of oral administration of a cGMP pilot lot of dmLT has been documented both in a preclinical GLP toxicology study and in an ongoing clinical study in the United States.

Here, the inventors demonstrate the efficacy a novel ETEC vaccine comprising dmLT adjuvant to enhance immuno responses.

The presently disclosed vaccine has particular benefits regard to its ability to effectively elicit immuno responses (in particular, to several CFs simultaneously) while keeping the amount of cells per unit dose sufficiently low to avoid adverse effects. Too large numbers of cells lead to adverse effects such as nausea and vomiting, in particular in infant subjects.

Certain aspects of the present invention have been disclosed by the inventors in an earlier academic publication (Svennerholm A M. From cholera to enterotoxigenic *Escherichia coli* (ETEC) vaccine development. Indian J Med Res. 2011 February; 133(2):188-96. Review).

DEFINITIONS

In the context of the present disclosure, the terms below have the specified meanings.

The abbreviation ETEC refers to enterotoxigenic *Escherichia coli* bacteria.

The term killed whole cell vaccine refers to vaccine containing whole (intact) but killed (non-living) bacteria.

The term unit dose refers to the combination of constituents intended for administration to a single subject at one given occasion, such as primary immunization or booster immunization.

The synonymous terms LCTBA, LCTBA-protein and LCTBA hybrid protein refer to a hybrid protein between the B-subunit of the *E. coli* heat-labile enterotoxin (LTB) and the B-subunit of the cholera toxin (CTB). Seven amino acids in the CTB molecule have been replaced by amino acids at corresponding positions of the LTB molecule. For details, see Lebens et al. 1996 (Lebens M, Shahabi V, Bäckström, et al. 1996. Synthesis of hybrid molecules between heat-labile enterotoxin and cholera toxin B subunits: potential for use in a broad spectrum vaccine. Infect Immun 64:2144-2150.)

The term dmLT refers to a non-toxic mutant of the LT toxin from *E. coli*. This molecule has been mutated in two different positions; a substitution of G for R at position 192, and L for A at position 211 and has been characterized by Norton et al. 2011 (Norton E B, Lawson L B, Freytag L C, Clements J D. Characterization of a mutant *Escherichia coli* heat-labile toxin, LT(R192G/L211A), as a safe and effective oral adjuvant. Clin Vaccine Immunol. 2011 April; 18(4): 546-51.)

The term non-antibiotic selection marker refers to genetic selection markers for selection of plasmids not requiring the use of antibiotics in the selection process. Examples include thyA complementation.

SUMMARY OF THE INVENTION

Figure 1:
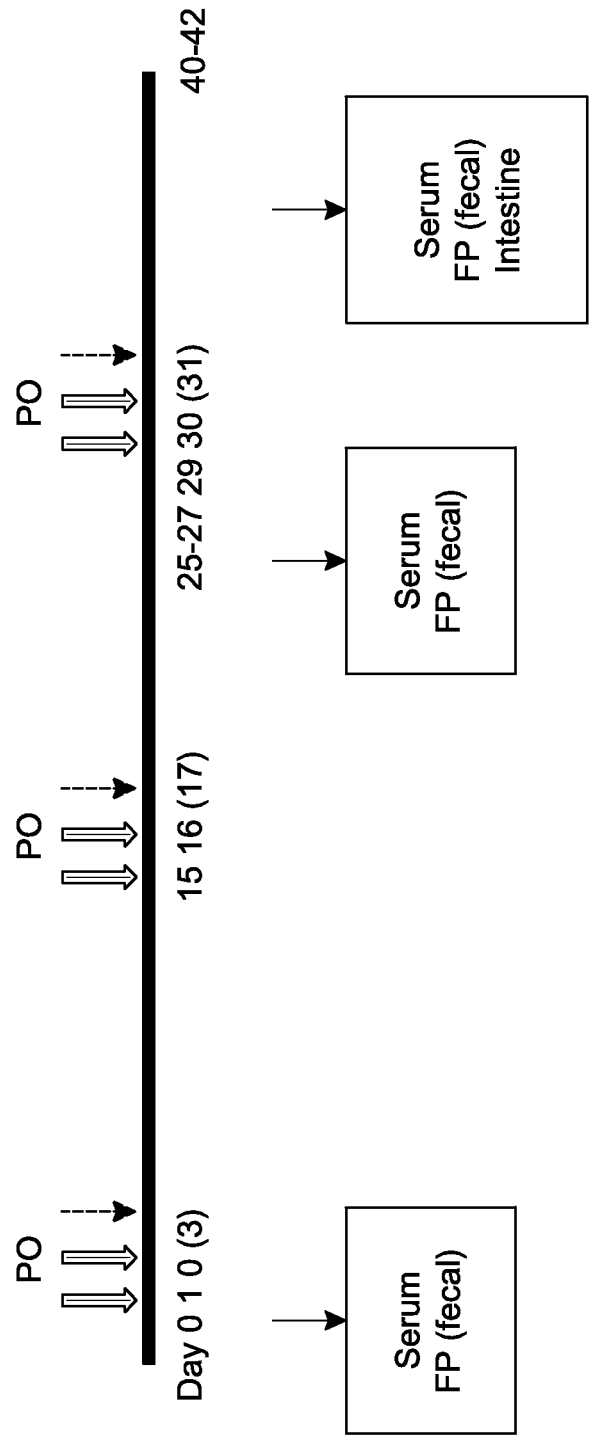
FIG. 1: Illustration of the design of the immunization studies in mice

In a first aspect there is provided an oral vaccine for immunization against ETEC-induced diarrhea, comprising inactivated Escherichia coli (E. coli) cells expressing an ETEC colonization factor antigen, LCTBA-protein and dmLT protein, wherein the vaccine preferably comprises less than $10^{13}$ cells per unit dose.

Said vaccine may comprise:
a) inactivated E. coli expressing CFA/I, preferably comprising a recombinant plasmid expressing the entire CFA/I operon under e.g. a tac promotor and having a non-antibiotic selection marker, most preferably strain ETEX21;
b) inactivated E. coli expressing CS3, preferably comprising a recombinant plasmid expressing the entire CS3 operon under e.g. an rns promotor being in turn under the lac operator and having a non-antibiotic selection marker, most preferably strain ETEX22;
c) inactivated E. coli expressing CS5, preferably comprising a recombinant plasmid expressing the entire CS5 operon under e.g. a tac promotor and having a non-antibiotic selection marker, most preferably strain ETEX23; and
d) inactivated E. coli expressing CS6, preferably comprising a recombinant plasmid expressing the entire CS6 operon under e.g. a tac promotor and having a non-antibiotic selection marker, most preferably strain ETEX24.

The vaccine may comprise per unit dose:
a) inactivated E. coli expressing CFA/I in an amount of 415-1245 ug (preferably 747-913 ug) of CFA/I;
b) inactivated E. coli expressing CS3 in an amount of 1485-4455 ug (preferably 2673-3267 ug) of CS3;
c) inactivated E. coli expressing CS5 in an amount of 255-765 ug (preferably 459-561 ug) of CS5;
d) inactivated E. coli expressing CS6 in an amount of 60-180 ug (preferably 108-132 ug) of CS6; and
e) LCTBA-protein in an amount of 500-1500 μg (preferably 900-1100 μg).

Preferably, the vaccine comprises per unit dose 1-200 μg dmLT, preferably 5-50 μg, more preferably 8-30 μg.

Preferably, the vaccine comprises per unit dose less than $10^{12}$ bacterial cells, more preferably less than $2\times10^{11}$ bacterial cells per unit dose.

Preferably, the vaccine comprises E. coli cells expressing CS6 having been inactivated with a method involving the use of phenol, preferably at a concentration of 0.6-2.0 percent by weight in an aqueous solution.

In a second aspect, there is provided a vaccine according to any of the preceding claims, for use in a procedure comprising oral administration of the vaccine to a subject to be immunized on at least two separate occasions separated in time by at least 3 days. Preferably, the occasions are separated in time by 3-60 days, more preferably 5-21 days, most preferably, 7-10 days.

Also disclosed is a method for immunizing a subject against ETEC-induced diarrhea, comprising administering a vaccine of the invention to the subject to be immunized on at least two separate occasions separated in time by at least 3 days. Preferably, said occasions are separated in time by 3-60 days, more preferably 5-21 days, most preferably, 7-10 days.

DETAILED DESCRIPTION

The present invention discloses an oral vaccine for immunization against ETEC-induced diarrhea, comprising inactivated Escherichia coli cells expressing an ETEC colonization factor antigen, LCTBA hybrid protein and dmLT protein. Preferably, the vaccine comprises less than $10^{13}$ cells per unit dose.

Preferably, the vaccine comprises the following components:
a) inactivated E. coli expressing CFA/I;
b) inactivated E. coli expressing CS3;
c) inactivated E. coli expressing CS5;
d) inactivated E. coli expressing CS6;
e) hybrid protein LCTBA; and
f) dmLT protein adjuvant.

More preferably, the components a)-d) are as specified below:
a) the inactivated E. coli expressing CFA/I is of a strain comprising a recombinant plasmid expressing the entire CFA/I operon under e.g. a tac promotor and having a non-antibiotic selection marker;
b) the inactivated E. coli expressing CS3 is of a strain comprising a recombinant plasmid expressing the entire CS3 operon under e.g. an rns promotor being in turn under the lac operator and having a non-antibiotic selection marker;
c) the inactivated E. coli expressing CS5 is of a strain comprising a recombinant plasmid expressing the entire CS5 operon under e.g. a tac promotor and having a non-antibiotic selection marker; and
d) the inactivated E. coli expressing CS6 is of a strain comprising a recombinant plasmid expressing the entire CS6 operon under e.g. a tac promotor and having a non-antibiotic selection marker.

More preferably, the components a)-d) are as specified below (see Examples for disclosure of the strains).
a) the inactivated E. coli expressing CFA/I is of strain ETEX21;
b) the inactivated E. coli expressing CS3 is of strain ETEX22;

c) the inactivated *E. coli* expressing CS5 is of strain ETEX23; and d) the inactivated *E. coli* expressing CS6 is of strain ETEX24

The vaccine may comprise per unit dose the following amounts of the specified components:

a) inactivated *E. coli* expressing CFA/I in an amount of 200-2000 ug of CFA/I;

b) inactivated *E. coli* expressing CS3 in an amount of 500-10000 ug of CS3;

c) inactivated *E. coli* expressing CS5 in an amount of 100-2000 ug of CS5;

d) inactivated *E. coli* expressing CS6 in an amount of 20-600 ug of CS6; and e) hybrid protein LCTBA in an amount of 200-5000 µg.

The vaccine may comprise per unit dose the following amounts of the specified components:

a) inactivated *E. coli* expressing CFA/I in an amount of 415-1245 ug of CFA/I;

b) inactivated *E. coli* expressing CS3 in an amount of 1485-4455 ug of CS3;

c) inactivated *E. coli* expressing CS5 in an amount of 255-765 ug of CS5;

d) inactivated *E. coli* expressing CS6 in an amount of 60-180 ug of CS6; and e) hybrid protein LCTBA in an amount of 500-1500 µg.

Most preferably however, the amounts are as specified below:

a) inactivated *E. coli* expressing CFA/I in an amount of 747-913 ug of CFA/I;

b) inactivated *E. coli* expressing CS3 in an amount of 2673-3267 ug of CS3;

c) inactivated *E. coli* expressing CS5 in an amount of 459-561 ug of CS5;

d) inactivated *E. coli* expressing CS6 in an amount of 108-132 ug of CS6; and e) hybrid protein LCTBA in an amount of 900-1100 µg.

Preferably, the vaccine may comprise 1-200 µg of the dmLT protein per unit dose, more preferably 5-50 µg and most preferably 8-30 µg.

Preferably, the vaccine comprises less than $10^{12}$ bacterial cells per unit dose. More preferably, the vaccine comprises less than $2 \times 10^{11}$ bacterial cells per unit dose. Most preferably, there are no more than $10^{11}$ bacterial cells per unit dose.

Preferably, the *E. coli* cells expressing CS6 of the vaccine have been inactivated with a method involving the use of phenol. In particular, the inactivation may have been performed using phenol at a concentration of 0.6-2.0 percent by weight in an aqueous solution.

The disclosed vaccine may be for use in a procedure comprising oral administration of the vaccine to a subject to be immunized on at least two separate occasions separated in time by at least 3 days. Preferably, the occasions are separated in time by 3-60 days, more preferably 5-21 days, most preferably, 7-10 days.

The vaccine is preferably administered formulated in a sodium bicarbonate solution to neutralize gastric acidity upon ingestion of vaccine.

All references are hereby incorporated by reference.

EXAMPLES

Example 1

Physical, Chemical and Pharmaceutical Properties and Formulation

General Background

The tetravalent vaccine consists of four inactivated recombinant *E. coli* strains (ETEX 21-24) expressing the CFs CFA/I, CS3, CS5, and CS6+ the hybrid protein LCTBA. The LCTBA component of this vaccine is identical to the LCTBA component used in the Prototype vaccine recently tested the in the phase I trial (study no. OEV-120). The dmLT component is identical to the lot used in the animal toxicology study and in an ongoing clinical phase I safety/immunogenicity study in the United States.

Inactivated *E. coli* CFA/I, Strain ETEX 21

The *E. coli* ETEX 21 strain was developed using a recombinant plasmid expressing the entire CFA/I operon under a tac promotor as described, with the difference that the antibiotic selection marker (ampicillin) was replaced with the gene encoding thymidinylate synthetase (thyA) from *V. cholerae* (Tobias, J., Lebens, M., Bölin, I., Wiklund, G., Svennerholm, A.-M. 2008. Construction of non-toxic *Escherichia coli* and *Vibrio cholerae* strains expressing high and immunogenic levels of enterotoxigenic *E. coli* colonization factor I fimbriae. Vaccine 26:2144-2150). The bacterial host for this host is an *E. coli* CFA/I, O:78, K strain. The strain was originally isolated in 1985 from a patient in Dhaka, Bangladesh, suffering from diarrhea due to an ETEC infection. This strain was used as a component of the first generation ETEC vaccine and has been given to at least 2,000 volunteers. The plasmid(s) encoding the ST and CFA/I native genes were removed by natural selection. Further modification was done by knocking out the thyA gene on the chromosome by inserting a kanamycin resistance gene in the thyA gene. Furthermore, in a second round of chromosomal deletion, the kanamycin gene was deleted in its first 200 nucleotides together with 200 nucleotides from the thyA gene making it kanamycin sensitive. The combination of the thyA-expressing plasmid and the thyA-deficient host strain enables antibiotic-free selection of the recombinant ETEX 21 strain.

Detailed Description of the Expression Vector for *E. coli* ETEX 21

The cfa operon was amplified by Polymerase chain reaction (PCR) from the wild-type ETEC strain No 325542. Amplification was carried out with a forward primer 5'CGGTCTCGAATTCTGATGGAAGCTCAGGAGG3' (SEQ ID NO: 1) and a reverse primer 5'CGGTCTCAAGCTTTCTAGAGTGTTTGACTACTTG3' (SEQ ID NO: 2). The forward primer was homologous to sequence 22 bp upstream of cfaA and the reverse primer incorporated the stop codon for cfaE. The resulting fragment carried the genes cfaABCE, all of which are necessary for production and assembly of CFA/I fimbriae. The PCR fragment was cloned in an expression vector based on the pACYC177 plasmid with the p15A origin of replication. After further replacement of antibiotic selection markers and introduction of a thyA gene from *V. cholerae* the resulting was electroporated into the host strain *E. coli* C600 ΔthyA Inactivated *E. coli* CS3, Strain ETEX 22

The *E. coli* ETEX 22 strain was developed using a recombinant plasmid expressing the entire CS3 operon under an rns promotor which in turn is under the lac operator. The selection system for this plasmid is also based on the thyA gene from *V. cholerae*. The bacterial host for this construct is the same *E. coli*, CFA/I, O78, K strain, as described for ETEX21. The combination of the thyA expressing plasmid and the thyA deficient host strain enables antibiotic-free selection of the recombinant ETEX 22 strain.

Detailed Description of the Expression Vector for *E. coli* ETEX 22

The entire operon encoding the CS3 fimbriae was cloned from *E. coli* strain SBL 107 as a HindIII fragment into the cloning vector pBluescript II SK+. The operon was then subcloned into a custom made expression vector, pNC-4 built on a p15A origin of replication, containing the $lacI^q$ gene, the thyA gene from *Vibrio cholerae*, the lac operator and downstream of this the rns gene from *E. coli*. The ms gene activates the CS1, CS2 and CS3 genes. Expression of rns is controlled by the lac operon thus enabling induction of CS3 expression by the addition of Isoprpoyl-β-D-galactopyranoside (IPTG).

Inactivated *E. coli* CS5, strain ETEX 23

The *E. coli* ETEX 23 strain was developed using a recombinant plasmid expressing the entire CS5 operon under a under a tac promotor. The selection system for this plasmid is also based on the thyA gene from *V. cholerae*. The bacterial host for this construct is the same *E. coli*, CFA/I, O78, $K^-$ strain, as described for ETEX 21 and ETEX 22. The combination of the thyA expressing plasmid and the thyA deficient host strain enables antibiotic-free selection of the recombinant ETEX 23 strain Detailed Description of the Expression Vector for *E. coli* ETEX 23

PCR was first applied to amplify a DNA fragment carrying the entire operon of CS5, i.e. csfA, csfB, csfC, csfE, csfF, and csfD, from the wild-type ETEC strain E17018/A (CS5+, CS6+, ST+). Template DNA was prepared by taking a fresh colony of E17018/A from an CFA agar plate and suspending the bacterial cells in 100 µl H20. The suspension was boiled in a water bath for 5 min and subsequently spun at full speed in a bench top centrifuge for 5 min. One µl aliquot of the resulting supernatant was used as DNA template in PCR. Amplification was carried out using forward (5'-CGGTCTCGAATTCTGCCAGAAAAGTTCATGCAG) (SEQ ID NO: 3) and reverse (5'-CGGTCTCAAGCTTCACCCTGACGGACAAAGATT) (SEQ ID NO: 4) primers (Eurofins MWG operon, Ebersberg, Germany), and the Expand High Fidelity PCR System (Roche Diagnostics GmbH). Forward primer is homologous to sequence 314 bp upstream of csfA and carries restriction sites for EcoRl and Eco31I, whereas the reverse primer, which is homologous to sequence 490 bp downstream of csfD, carries restriction sites for HindIII and Eco31I, at the 5' end. PCR conditions were as follow: 95° C. for 5 min, 31 cycles of 94° C. for 15 s, 58° C. for 30 s and 68° C. for 5 min and 30 sec, with a final extension of 7 min at 72° C. The PCR reaction contained 10 mM of each dNTPs, 25 pmole of each primer, and ca. 5 units of the Expand High Fidelity Enzyme. The resulting 7022 bp fragment carries the genes csfABCDEF, all of which are necessary for production and assembly of CS5.

Secondly, the plasmid pJT(MT)-CFA/I-thyA-15Aori was restricted with EcoRl and HindIII, resulting in a 3838 bp fragment containing Laclq-thyA-15Aori.

Thirdly, the both above prepared fragments were then ligated using T4 DNA ligase (New England Biolabs, In vitro Sweden AB, Stockholm, Sweden), resulting in pJT-CS5-thyA-15Aori (10860 bp).

Fourthly, the constructed plasmid pJT-CS5-thyA-15Aori was then electroporated into thymine dependent *E. coli* C600 strain (SBL/Crucell Vaccines). A recombinant C600 clone expressing CS5 was selected on the basis of thymine independence.

Inactivated *E. coli* CS6, Strain ETEX 24

The *E. coli* ETEX 24 strain was developed using a recombinant plasmid expressing the entire CS6 operon under a tac promotor. The selection system for this plasmid is also based on the thyA gene from *V. cholerae*. The bacterial host for this construct is an *E. coli* K12 strain C600, previously used as a placebo in numerous Dukoral® and ETEC clinical trials. This strain was modified by knocking out the thyA gene on the chromosome and inserting a kanamycin resistance gene in the thyA gene. This strain was used as host for the SBL109 strain, studied in a previous clinical trial as a component of the "Prototype ETEC Vaccine No 2" (study no OEV-120; EudraCT:2009-015741-23). In a second round of chromosomal deletion the kanamycin gene was deleted in its first 200 nucleotides together with 200 nucleotides from the thyA gene making it kanmycin sensitive. The combination of the thyA expressing plasmid and the thyA deficient host strain enables antibiotic-free selection of the recombinant ETEX 24 strain.

Detailed Description of the Expression Vector for *E. coli* ETEX 24

PCR was first applied to amplify the genes of the entire operon of CS6, i.e. cssA, cssB, cssC, and cssD, from ETEC strain GB35(CS6+, LT+). Template DNA was prepared from freshly grown colonies taken from CFA plates as described above. One µl aliquots of the resulting supernatant were used as DNA template in PCR. Amplification was carried out using forward and reverse primers (Nicklasson et al, 2006; Eurofins MWG operon, Ebersberg, Germany), and the Expand High Fidelity PCR System (Roche Diagnostics GmbH). The forward primer (5'-CGGTCTCGAATTCCACTCACCAATAAAAGCRTCAATACG) (SEQ ID NO: 5), which is upstream the cssA carries restriction sites for and Eco31I and EcoRl, whereas the reverse primer (5'-CGGTCTCAAGCTTAACATTGTTTATTTACAACAGATAATTGTTTG) (SEQ ID NO: 6), which is downstream the cssD, carries restriction sites for Eco31I and HindIII, at the 5' end. PCR conditions were as follows: 95° C. for 5 min, 32 cycles of 94° C. for 15 s, 58° C. for 30 s and 68° C. for 3.5 min, with a final extension of 7 min at 72° C. The PCR reaction contained 10 mM of each dNTPs, 25 pmole of each primer, and ca. 5 units of the Expand High Fidelity Enzyme. The amplified fragment was then digested with Eco31I, resulting in a fragment flanked with EcoRl and HindII sites.

Secondly, the previously constructed plasmid pJT-CS2-Cm (containing the chloramphenicol marker cat) was restricted with EcoRl and HindIII. The fragment containing the entire plasmid without the CS2 operon, i.e. pJT-Cm-ΔCS2 was then gel-extracted (using appropriate kit from Qiagene).

Thirdly, PCR fragment and the gel extracted fragment from the pervious sections were then ligated using T4 DNA ligase (New England Biolabs, In vitro Sweden AB, Stockholm, Sweden), and resulted in a 8077 bp plasmid, pJT-CS6-Cm, harboring the CS6 operon located downstream the IPTG-induced tac promoter.

Fourthly, the plasmid pJT-CS6-Cm was then cleaved with the restriction enzymes AvrII and XhoI, resulting in a 6992 bp fragment containing laclq, tec promoter, and the CS6 operon, i.e. pJT-CS6-ΔCm. This fragment was then gel-extracted (using appropriate kit from Qiagene).

Fifthly, preparation of ThyA: The plasmid pNC-4 WC was used in a PCR reaction to amplify the thyA. The forward primer, (5'-CGGTCTCCCTAGGCCTCCTTACCTATGGT- GATC) (SEQ ID NO: 7) is homologous to a sequence starting 98 bp upstream of thyA and carries restriction sites for Eco31I and AvrII, whereas the reverse primer (5'-CGGTCTCCTCGAGCGACTCTAGACCTAACCG) (SEQ ID NO: 8), which is homologous to a sequence ending 75 bp downstream of thyA, and carries restriction sites for Eco31I and XhoI, at the 5' end. PCR conditions were as follows: 95° C. for 5 min, 31 cycles of 94° C. for 15 s, 58° C. for 30 s and 72° C. for 50 sec, with a final extension of 7 min at 72° C. The resulting 1065 bp fragment containing thyA, was then gel-extracted and cleaved with XhoI and AvrII.

Sixthly, the prepared fragment of thyA and the fragment pJT-CS6-ΔCm, both having flanking sites for XhoI and AvrII were then ligated, and resulted in a 8057 bp plasmid, called pJT-CS6-thyA-15Aori.

Finally, the constructed plasmid pJT-CS6-thyA-15Aori (8057 bp) was then electroporated into thymine dependent *E. coli* C600 strain. A recombinant C600 clone expressing CS6 was then selected on the basis of thymine independence.

LCTBA Protein

LCTBA is a hybrid protein between the B-subunit of the *E. coli* heat-labile enterotoxin (LTB) and the B-subunit of the cholera toxin (CTB). Seven amino acids in the CTB molecule have been replaced by amino acids at corresponding positions of the LTB molecule (Lebens M, Shahabi V, Bäckström M, et al. 1996. Synthesis of hybrid molecules between heat-labile enterotoxin and cholera toxin B subunits: potential for use in a broad spectrum vaccine. Infect Immun 64:2144-2150). The LCTBA encoding DNA was cloned on a plasmid under a tac promotor. The LCTBA used in this study had the amino-acid sequence of SEQ ID NO: 9. The plasmid has the thyA gene from *E. coli* and is expressed in a *V. cholerae* strain that is deleted in its thyA gene, enabling antibiotic free selection of this plasmid. The *V. cholerae* strain that hosts the plasmid is a further development of the strain holding the rCTB213 encoding plasmid JS1569. The change is the deletion of the thyA gene, thus the genetic characteristics are ΔctxA, ΔthyA, Δkan. The LCTBA protein was recently evaluated for safety and immunogenicity in 1 mg and 4 mg dosages together with inactivated SBL109 bacteria in the OEV-120 study. This study revealed that the LCTBA protein was safe and strongly immunogenic at both dosage levels (see below).

dmLT (R192G/L211A) Protein Adjuvant

Initially, a mutant LT toxoid ("mLT," LT(R192G)) was constructed by substitution of arginine with glycine at position 192 of the A subunit (Norton E B, Lawson L B, Freytag L C, Clements J D. Characterization of a mutant *Escherichia coli* heat-labile toxin, LT(R192G/L211A), as a safe and effective oral adjuvant. Clin Vaccine Immunol. 2011 April; 18(4):546-51.). This genetic modification eliminated the ability of subunit A to be activated by trypsin cleavage and greatly reduced the enzymatic and biological activity of the toxin. Further attenuation was accomplished by adding a second substitution, leucine to alanine at position 211. The double mutant toxoid induced no detectible fluid accumulation when given to mice by the intragastric route, while retaining immunogenicity and adjuvanticity.

Stability of Test Vaccine

Monovalent bulk preparations of *E. coli* strains ETEX 21-24 stored at 4° C. and 20° C. are tested in an ongoing stability study. The monovalent bulk preparations have so far been shown to be stable for at least 3 months. The study will continue for 48 months.

LCTBA hybrid protein purified from a 500-liter fermentor culture, is also subjected to an ongoing stability study. The preparation is stored at 4° C. and 25° C. for a period of 48 months. The same material is also stored at −65° C. for reference purpose. So far, the protein has been shown to be stable for at least 24 months, irrespective of storage temperature.

The adjuvant dmLT is included in an ongoing 30-months stability study. Lyophilized vials are stored at −20° C. The protein has been shown to be stable for at least 24 months.

A stability study of the complete Tetravalent vaccine, stored at 4° C. and 20° C. is ongoing. QC analyses indicate that the vaccine is stable for at least 3 months. The study will continue for 48 months.

Formulation

Tetravalent Oral ETEC Vaccine

| | |
|---|---|
| *E. coli* CFA/I, ETEX21 | 830 μg in approx. 20 × $10^9$ bacteria |
| *E. coli* CS3, ETEX22 | 2,970 μg in approx. 20 × $10^9$ bacteria |
| *E. coli* CS5, ETEX23 | 510 μg in approx. 20 × $10^9$ bacteria |
| *E. coli* CS6 ETEX24 | 120 μg in approx. 20 × $10^9$ bacteria |
| Hybrid protein LCTBA | 1 mg |
| Phosphate-buffered saline | q.s. ad 8 ml |

The vaccine was produced by Unitech Biopharma, Matfors, Sweden

The ETEX21, ETEX22 and ETEX23 were inactivated using formalin treatment. For ETEX24 phenol was used for inactivation, since formalin treatment destroyed the CS6 antigen.

Briefly, a 500 liter fermentor was inoculated with an *E. coli* strain overexpressing the CS6 antigen (ETEX 24). After induction of expression by IPTG the fermentation was continued for 8 hours. The bacteria were harvested and washed over a 500 kD ultrafilter and finally dispensed at a concentration of 20×$10^9$ bacteria/ml. Phenol was added to a final concentration of 0.8% (w/v) and the suspension was kept at 20° C. for 40 hours under constant stirring. The suspension was washed over a 500 kD ultrafiltration membrane in phosphate buffered saline and stored at 4° C.

Inhibition ELISA to quantitate the amount of CS6 antigen was done on fresh material before inactivation and washed inactivated material. Surprisingly, the phenol inactivation not only retained CS6 immunoreactivity, but in fact increased it substantially (data not shown).

During the inactivation procedure samples were taken before inactivation after 1, 2, 18 and 40 hours of inactivation to test for viability. Briefly, samples taken were washed by centrifugation and resuspended in the original volume in PBS whereafter dilutions were made in PBS and plated on Colonisation Factor Agar (CFA agar). Plates were incubated at 37° C. and counted the following day.

Optional Adjuvant dmLT (where Relevant)

Lyophilized protein: 1 mg per vial

For use, the protein was reconstituted with 1 ml sterile water. The solution was further diluted to 10 μg or 25 μg in 1 ml saline solution. The protein dmLT was manufactured at the Pilot Bioproduction Facility, Walter Reed Army Institute of Research in Forest Glen, Md. USA.

Sodium Bicarbonate Buffer Powder

The buffer is to be used to neutralize gastric acidity upon ingestion of vaccine. The buffer is also used as placebo in the study. The dried powder is supplied in moisture-proof sachets (5.6 g/sachet).

Sodium Bicarbonate buffer Powder:

| | |
|---|---|
| Sodium hydrogen carbonate | 3 600 mg |
| Citric acid, anhydrous | 1 450 mg |
| Sodium carbonate | 400 mg |
| Rasberry flavor | 70 mg |
| Sodium saccharin | 30 mg |

For use, the carbonate buffer is dissolved in 150 ml of potable water.

The Sodium hydrogen carbonate buffer was produced by Recip AB in Sweden.

Example 2

Preclinical Efficacy

Immunogenicity of Enhanced Tetravalent ETEC Vaccine in Mice and Adjuvant Effect of dmLT Extensive preclinical studies in mice have been undertaken to evaluate the immunogenicity of the different versions of the new oral ETEC vaccine, the monovalent Prototype vaccine and the final Tetravalent vaccine, especially the ability to generate IgA antibodies in intestine after oral/intragastric immunization and the effect of co-administration of the dmLT adjuvant on the immune responses.

These vaccines, given alone or together with dmLT in doses of up to ca $1 \times 10^9$ bacteria and 25 µg dmLT per immunization round were tested in mice after two or three rounds of oral immunizations for possible adverse reactions and for their capacity to induce serum and intestinal-mucosal antibody responses to the different vaccine components.

Mouse Immunizations and sample collection. Groups of female Balb/C and C57 Bl/5 mice (Charles River; 6-8 weeks of age; 5 mice/group) were used for oral (intragastric) immunizations. All mice were given two doses two days apart in 0.3 ml 3% sodium bicarbonate solution intragastrically through a baby feeding catheter (first round of immunization), followed two weeks later by two identical immunizations two days apart in a second round of immunization. Bleedings were performed before the first immunization and two weeks after the last immunization, at which times fecal pellets (FPs) were also collected and extracts prepared as described previously (Nygren E, Holmgren J, Attridge S R. Murine antibody responses following systemic or mucosal immunization with viable or inactivated *Vibrio cholerae*. Vaccine 2008; 26:6784-90). In addition, at the later time point when the mice were sacrificed, they were perfused with a heparin-PBS solution to remove blood from the tissues, and small intestinal tissue collected and extracted with a 2% (w/v) Saponin-PBS solution (the Perfext method) as described previously Villavedra M, Carol H, Hjulstrom M, Holmgren J, Czerkinsky C. "PERFEXT": a direct method for quantitative assessment of cytokine production in vivo at the local level. Res Immunol 1997; 148:257-66).

ELISAs. IgG+IgM and IgA antibody titers were determined in sera, fecal and intestinal extracts, by ELISA, as described previously (Rudin A, Svennerholm A-M. Colonization factor antigens (CFAs) of enterotoxigenic *Escherichia coli* can prime and boost immune responses against heterologous CFAs. Microb Pathog 1994; 16:131-9). CS6, for use as coating antigen (at the final concentration of 0.7 µg/ml) in the relevant ELISAs, was purified from the previously described TOP10-CS6 over-expressing strain (Tobias J, Lebens M, Källgård S, Nicklasson M, Svennerholm A-M. Vaccine 2008; 26:5373-80.), by sequential ammonium sulphate precipitation and gel filtration. Sera from individual mice were tested using low-binding microtiter plates (Greiner), and samples were initially diluted 1/100 followed by serial three-fold dilutions. Fecal pellet extracts and small intestine tissue extracts were tested in high-binding microtiter plates (Greiner) in 3-fold serial dilutions from a starting dilution of ⅓. Antibody titers were calculated as the reciprocals of the sample dilutions which gave an A450 absorbance of 0.4 above the background value. In the fecal and intestinal extract samples, total IgA was also measured by ELISA as described (Nygren E, Holmgren J, Attridge S R. Vaccine 2008; 26:6784-90), and antigen-specific IgA antibody values were expressed as IgA titer units per µg of total IgA.

Summary of Results

The results in summary showed that: 1) the vaccines, both when given alone and when combined with dmLT, were well tolerated; 2) the vaccines also induced strong serum as well as intestinal antibody responses to each of the antigens included in the vaccines, exceeding the responses achieved with vaccine preparations corresponding to the previous first-generation oral ETEC vaccine;

and 3) the co-administration of dmLT increased (adjuvanted) especially the intestinal and less pronounced also the serum antibody responses to each of the antigens in the vaccines. These findings are illustrated by the results shown in FIGS. 2-4.

Figure 2:
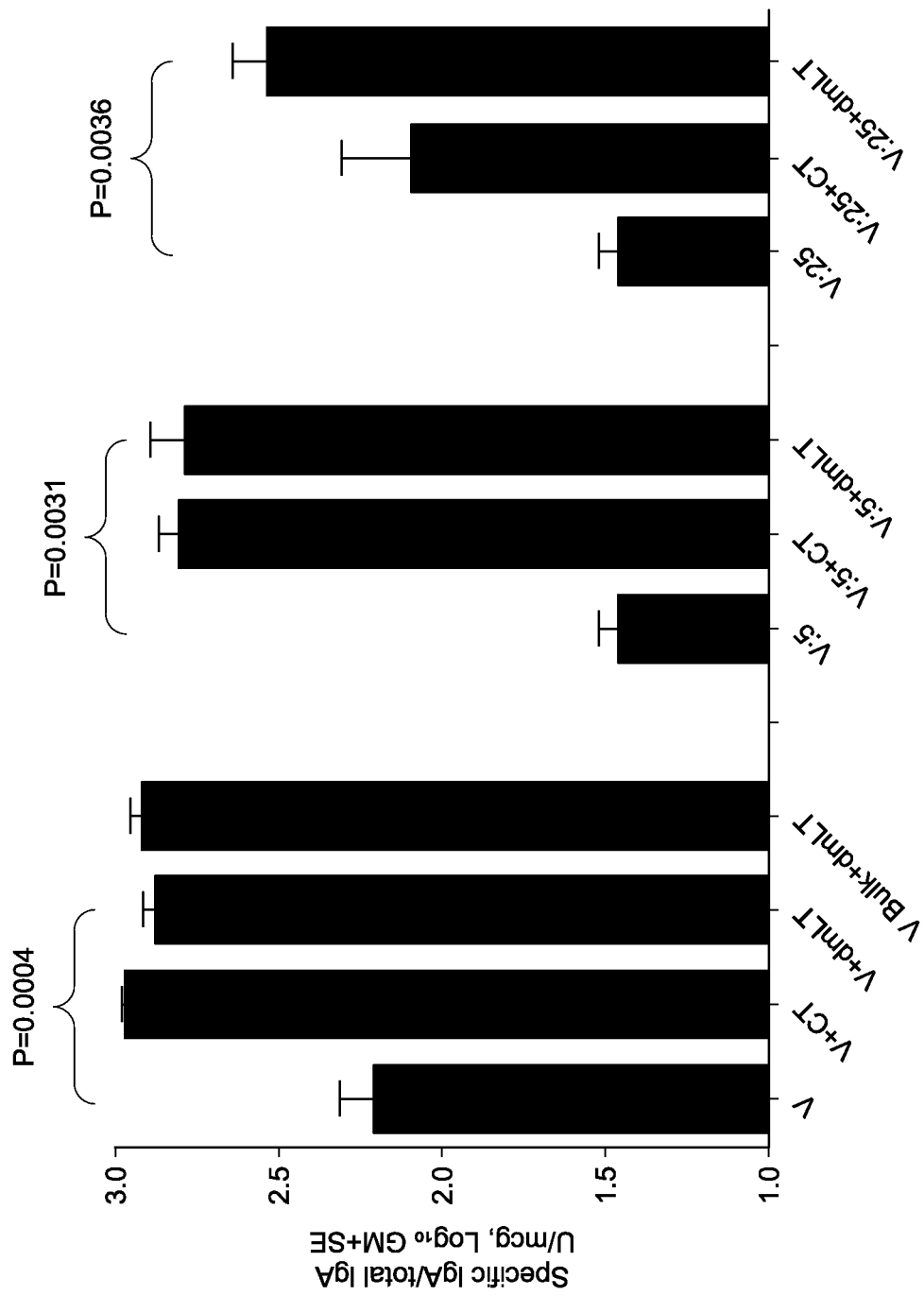
FIG. 2: Comparable adjuvant activity of dmLT and cholera toxin (CT) for intestinal (fecal) IgA anti-CFA/I antibody response to orally administered formalin-killed recombinant E. coli overexpressing CFA/I. (V=clinical lot vaccine V109, tested in different dosages alone and with dmLT 25 μg or CT 15 μg)

In FIG. 2, an exemplifying experiment is shown where groups of Balb/c mice (5 animals per group) were immunized in two rounds with the monovalent Prototype vaccine in different doses either alone or together with 15 microgram cholera toxin (CT) or 25 microgram dmLT per round, and IgA anti-CFA/I responses in fecal extracts examined 10 days after the last immunization. The vaccine doses given per round (divided up in half on two consecutive days) corresponded to $1 \times 10^9$ formalin-killed bacteria+5 microgram LCTBA ("V"), one-fifth ("V:5") or one-twenty-fifth ("V: 25") of this dose; yet another group were immunized with the higher dose of the whole-cell vaccine preparation without any added LCTBA together with dmLT ("V Bulk+ dmLT"). The results show that the vaccine in a dose-dependent manner by itself induced an intestinal-fecal IgA anti-CFA/I response, which was significantly further increased/adjuvanted by co-administration of vaccine with dmLT, and also that the dmLT adjuvant effect was most pronounced for lower vaccine doses, was fully comparable to that of CT, and did not depend on the presence of LCTBA in the vaccine.

Figure 3:
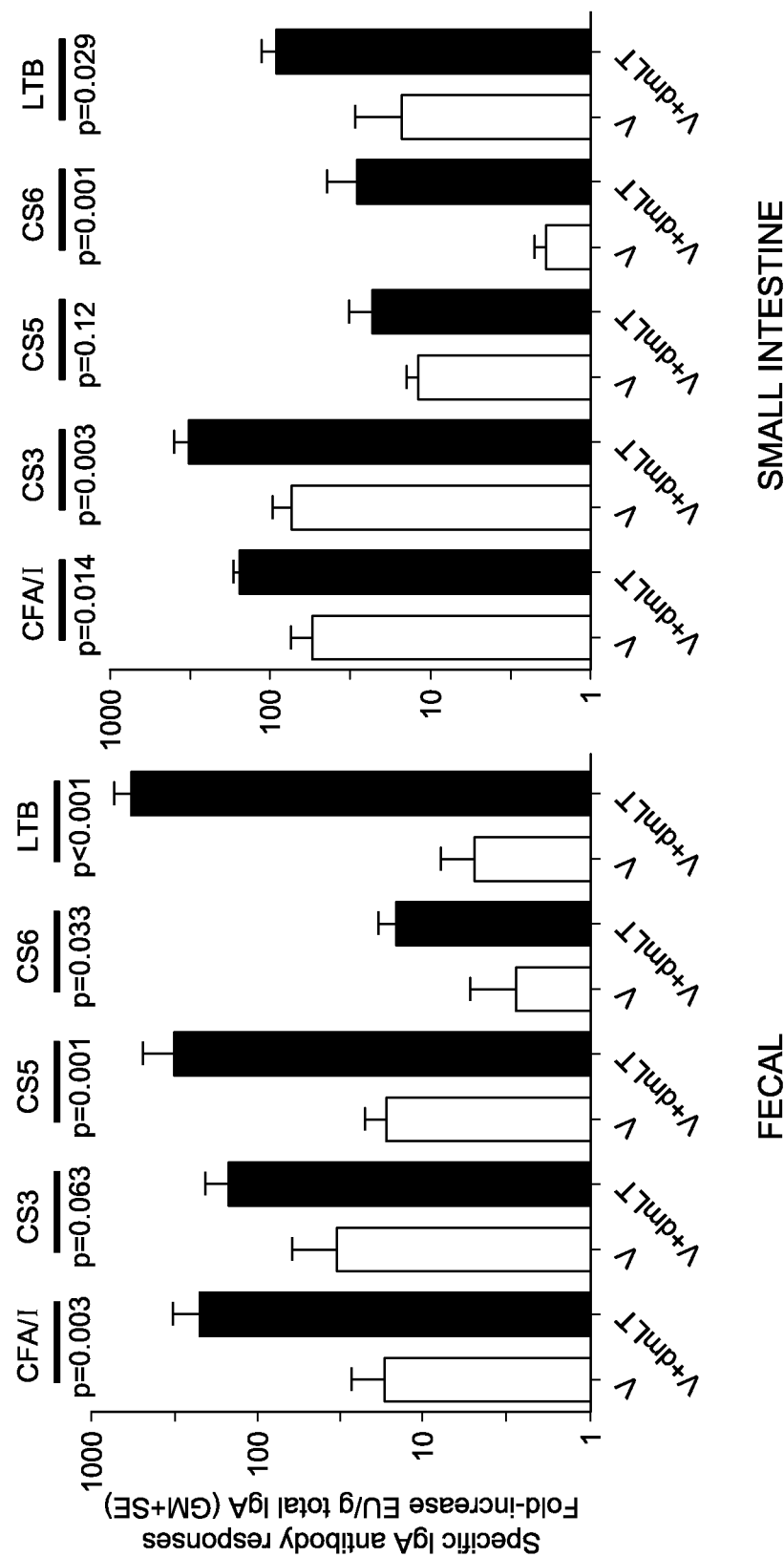
FIG. 3: Oral immunization in mice with tetravalent ETEC vaccine (V) induces fecal and small intestinal IgA antibody responses to all vaccine components, that are further enhanced by co-administering vaccine with dmLT adjuvant (V+dmLT). Log 10 fold-increase responses over mean background in unimmunized mice are shown. Responses are from Balb/c mice except for CS6 which are from C57/BI mice
Figure 4:
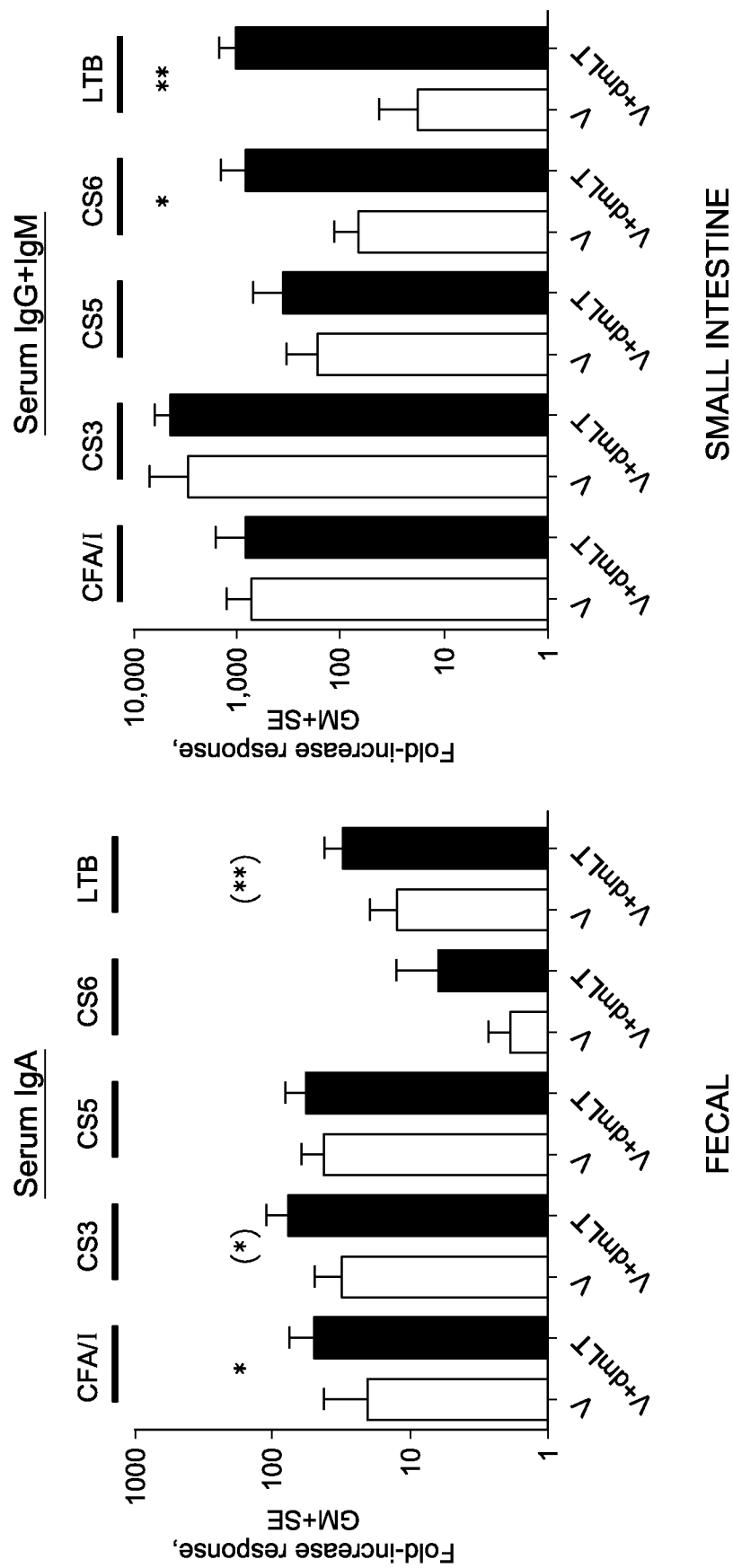
FIG. 4: Oral immunization in mice with tetravalent ETEC vaccine (V) induces strong serum IgA and IgG+IgM antibody responses to all vaccine components, that are often further enhanced by the dmLT adjuvant (V+dmLT). * $p<0.05$; ** $p<0.01$ refer to dmLT-induced difference in vaccine response; (*) & (**) $p<0.05$ & $<0.01$ in a repeat experiment. Responses are in Balb/c mice except for CS6 which are from C57/BI mice.

FIGS. 3 and 4 show results from another exemplifying experiment in which the Tetravalent ETEC vaccine, alone or together with dmLT, was administered in three rounds intragastrically to Balb/c and C57/BI mice, and intestinal (FIG. 3) antibody responses were measured 10-12 days after the last immunization and serum antibodies 10 days after completion of the second immunization round (FIG. 4). The vaccine dose used per round corresponded to $1 \times 10^9$ inactivated bacteria (i.e. $2.5 \times 10^3$ bacteria of each strain) and 10 microgram LCTBA, and the dmLT dose per round was 25 microgram. A group of unimmunized mice served as controls. The results show that the vaccine even without any adjuvant in comparison with the controls gave rise to 2- to 50-fold fecal or small intestinal IgA responses to each of the vaccine component antigens, and also that these responses were further significantly increased when the vaccine was administered together with the dmLT adjuvant (FIG. 3). Similarly, immunization with vaccine alone induced significant serum antibody responses to each of the tested antigens, both of IgA and even further pronounced of IgG+IgM isotypes; these responses in most cases were further enhanced by the dmLT component although the increases were not always statistically significant (FIG. 4). The results show the responses in Balb/c mice except for the anti-CS6 responses that are from C57/BI mice; the reason for this is that both this and other similar experiments have shown that the response to CS6 is stronger in C57/BI mice (ref Tobias et al 2011) while the response to the other components is similar or marginally higher in Balb/c mice.

Neutralization of LT Toxin with Serum Against LCTBA and CTB

LCTBA hybrid protein is expected to generate antibodies with a higher LT toxin neutralizing capacity as compared to CTB. Toxin neutralization was studied using purified LT toxin in Y1-adrenal cell assay. Briefly, rabbits were immunized s.c. on days 0, 13, and 28 with 30 µg LCTBA or CTB. Sera were collected two weeks post the last immunization. Neutralization of toxin was measured by incubating a fixed concentration of trypsin-treated LT toxin (1 ng/ml) with serial dilutions of serum. Remaining toxin, not neutralized by serum was measured using Y1-adrenal cell assay. Sera from rabbits immunized with LCTBA hybrid protein showed a stronger toxin neutralizing capacity as compared to sera from rabbits immunized with CTB (Table X).

TABLE X

Neutralization of *E. coli* LT toxin with rabbit serum against LCTBA hybrid protein and CTB, respectively, as measured using adrenal cell assay.

| Serum directed against | LT toxin neutralizing titer | |
|---|---|---|
| | Day 0 | Day 46 |
| LCTBA | <5 | ≥32 |
| CTB | <5 | 8 |

Example 3

Toxicology

Preclinical Safety and Immunogenicity of dmLT in Rats

In support of a dmLT Phase-I study, a GLP compliant toxicology study entitled "Repeat Dose Oral GLP Toxicology Study in Sprague-Dawley Rats of dmLT" was conducted by Spring Valley Laboratories Inc., Woodbine, Md., USA. Briefly, groups of rats (numbered 1-4) received one or two doses by gastric gavage of: 0.9% Saline (control, gr 1), 50 µg (gr 2), 100 µg (gr 3), or 200 µg dmLT(gr4). There were no test article-related adverse changes in mortality, body weights, organ weights, organ to body weight ratios or clinical observations. Histopathological observation also detected no definitive treatment—related effects in any of the groups. Increased globulin (groups 2, 3 and 4 females) and total protein (group 3 and 4 females) and decreased albumin/globulin (groups 2, 3 and 4 females) at 8 hours suggested a slight increase in acute phase alpha globulins. However at Day 17, similar findings were not observed indicating the transient nature of the change. No other treatment-related changes in clinical pathology parameters were evident.

The immune response was also evaluated in these animals by determining anti-LTB IgG levels by ELISA at four weeks after the Day 0 dosing. All animals receiving dmLT (at any dose level) mounted significant serum IgG responses to LTB; while all animals receiving the saline control were negative.

Toxicology of the Tetravalent Vaccine±dmLT Adjuvant in Mice

A repeated dose toxicity study of the Tetravalent vaccine with and without dmLT was conducted by Visionar A B, Uppsala, Sweden (Visionar Preclinical Study Report VP10-34-01). The mouse was chosen as experimental animal since most of the earlier preclinical research of the vaccine has been performed in mice. In total, 90 male mice and 90 female mice (strain C57BL/6J), were used in the study. The animals were given weight-adjusted oral administrations on two occasions with the tetravalent vaccine±5 µg or 25 µg dmLT/dose in a low and a high dose corresponding to 5 and 25 times clinical dose/kg body weight. In earlier preclinical GLP studies, the ETEC monovalent Prototype vaccine in a high dose (100× clinical dose/kg body weight) was found safe and was therefore included in this study as a comparator. The animals were divided into six groups and treated with phosphate-buffered saline solution (PBS), weight-adjusted doses of Control and Test Articles as described in Table 6. The preparations were administered in 250 µl-volumes by oral gavage on two different occasions with one week in between. One week after the last administration the animals were sacrificed and samples were taken for blood chemistry, histopathology and serology.

Control Article: Monovalent Prototype Vaccine

| | |
|---|---|
| *E. coli* SBL109: | 600 µg CFA/I in approx. 30 × $10^9$ inactivated bacteria |
| Hybrid protein LCTBA: | 1 mg |
| Phosphate-buffered saline: | q.s. ad 6.0 ml |

Test Article: Tetravalent Vaccine

| | |
|---|---|
| *E. coli* ETEX21 | 859 µg CFA/I in approx 20 × $10^9$ inactivated bacteria |
| *E. coli* ETEX22 | 3,851 µg CS3 in approx 20 × $10^9$ inactivated bacteria |
| *E. coli* ETEX23 | 1,100 µg CS5 in approx 20 × $10^9$ inactivated bacteria |
| *E. coli* ETEX24 | 120 µg CS6 in approx 20 × $10^9$ inactivated bacteria |
| Hybrid protein LCTBA: | 1 mg |
| Phosphate-buffered saline: | q.s. ad 8.0 ml |

TABLE 6

Study groups description. Vaccines were given as weight-adjusted doses

| Group | Test/Control article | Number of animals male/female |
|---|---|---|
| 1 | Control Article (PBS) | 15M/15F |
| 2 | Prototype vaccine; 100x clin dose | 15M/15F |
| 3 | Tetravalent vaccine; 5x clin dose | 15M/15F |
| 4 | Tetravalent vaccine; 5x clin dose + 25 µg dmLT | 15M/15F |
| 5 | Tetravalent vaccine; 25x clin dose | 15M/15F |
| 6 | Tetravalent vaccine; 25x clin dose + 625 µg dmLT | 15M/15F |

Although a few statistically significant differences were found between groups of male mice regarding WBC, RBC, HCT, HGB, and PLT, the differences were small and probably of no biological significance. No significant differences were observed between vaccine-treated groups of females. Between groups of males, animals treated with complete vaccine at 25× clinical dose showed higher concentrations of albumin and potassium than Comparator treated animals. The animals treated with tetravalent vaccine at 5× clinical dose+dmLT showed higher ALAT serum concentration than PBS-treated animals. Since there was no consistent effect on the clinical chemistry parameters analyzed among males and females and the differences between groups were small one may conclude that, albeit statistically significant, the observed differences probably have no biological significance. The immune responses to CFA/I and LCTBA were in agreement with earlier studies.

In conclusion, in comparison to PBS-treated animals, the vaccines in high doses affected the general health status of animals only slightly. However, no major pathological, clinical chemistry or hematological observations were found. The monovalent Prototype vaccine in 100× the clinical dose and the Tetravalent vaccine in a dose of 25× the clinical dose+dmLT caused similar effects on the general health status.

Example 4

Vaccine Administration to Humans

The vaccine shall be administered by the oral route only.

Four groups with 30 adult Swedish volunteers in each will be given Tetravalent vaccine, Tetravalent vaccine+10 ug dmLT, Tetravalent vaccine+25 ug dmLT or placebo.

Subjects randomized to the vaccine only group: The content of one vaccine vial is mixed with 150 ml reconstituted carbonate buffer solution prior to administration.

Subjects randomized to receive adjuvanted vaccine: The content of one vaccine vial and one vial of adjuvant (10 μg or 25 μg) are mixed with 150 ml reconstituted carbonate buffer solution prior to administration.

Placebo recipients: Only 150 ml reconstituted carbonate buffer solution.

To maintain blinding of the study, the test items (vaccine+/−adjuvant) and placebo will be prepared by an unblinded nurse who has no contact with the study participants. A blinded nurse will then administer the dose.

The invention claimed is:

1. An immunogenic composition, comprising inactivated *Escherichia coli* (*E. coli*) cells expressing:
   enterotoxigenic *E. coli* (ETEC) colonization factor antigens comprising:
      inactivated *E. coli* expressing colonization factor A/I (CFA/I) in an amount of 415-1245 μg per unit dose;
      inactivated *E. coli* expressing *Coli* surface antigen 3 (CS3) in an amount of 1485-4455 μg per unit dose;
      inactivated *E. coli* expressing *Coli* surface antigen 5 (CS5) in an amount of 255-765 μg per unit dose; and
      inactivated *E. coli* expressing *Coli* surface antigen 6 (CS6) in an amount of 60-180 μg per unit dose;
   a hybrid protein comprising a B-subunit of *E. coli* heat-labile enterotoxin (LTB) and a B-subunit of cholera toxin (CTB) (LCTBA-protein); and
   a double mutant heat-labile toxin (dmLT) protein,
   wherein the immunogenic composition comprises less than $10^{13}$ cells per unit dose and said immunogenic composition is formulated for oral administration.

2. The composition according to claim 1, comprising per unit dose 1-200 μg dmLT.

3. The composition according to claim 2, comprising per unit dose 5-50 μg dmLT.

4. The composition according to claim 3, comprising per unit dose 8-30 μg dmLT.

5. The composition according to claim 1, comprising less than $10^{12}$ bacterial cells per unit dose.

6. The composition according to claim 5, comprising less than $2 \times 10^{11}$ bacterial cells per unit dose.

7. The composition according to claim 1, wherein:
   a) the inactivated *E. coli* expressing CFA/I is of a strain comprising a recombinant plasmid expressing the entire CFA/I operon under a tac promotor and having a non-antibiotic selection marker;
   b) the inactivated *E. coli* expressing CS3 is of a strain comprising a recombinant plasmid expressing the entire CS3 operon under an rns promotor which is under the lac operator and having a non-antibiotic selection marker;
   c) the inactivated *E. coli* expressing CS5 is of a strain comprising a recombinant plasmid expressing the entire CS5 operon under a tac promotor and having a non-antibiotic selection marker; and
   d) the inactivated *E. coli* expressing CS6 is of a strain comprising a recombinant plasmid expressing the entire CS6 operon under a tac promotor and having a non-antibiotic selection marker.

8. The composition according to claim 1, comprising per unit dose LCTBA-protein in an amount of 500-1500 μg.

9. The composition according to claim 8, comprising per unit dose:
   a) inactivated *E. coli* expressing CFA/I in an amount of 747-913 μg of CFA/I;
   b) inactivated *E. coli* expressing CS3 in an amount of 2673-3267 μg of CS3;
   c) inactivated *E. coli* expressing CS5 in an amount of 459-561 μg of CS5;
   d) inactivated *E. coli* expressing CS6 in an amount of 108-132 μg of CS6; and
   e) LCTBA-protein in an amount of 900-1100 μg.

10. The composition according to claim 1, wherein the composition comprises *E. coli* cells expressing CS6 having been inactivated with a method comprising the use of phenol.

11. The composition according to claim 10, wherein the phenol is at a concentration of 0.6-2.0 percent by weight in an aqueous solution.

12. A method of eliciting an immune response in a subject comprising orally administering the composition according to claim 1 to the subject on at least two separate occasions separated in time by at least 3 days.

13. The method according to claim 12, wherein the occasions are separated in time by 3-60 days.

14. The method according to claim 13, wherein the occasions are separated in time by 5-21 days.

15. The method according to claim 14, wherein the occasions are separated in time by 7-10 days.

* * * * *